US010752637B2

(12) United States Patent
Lazeroms et al.

(10) Patent No.: US 10,752,637 B2
(45) Date of Patent: Aug. 25, 2020

(54) BIS-DIOX(OL)ANE COMPOUNDS

(71) Applicant: Koninklijke Coöperatie Cosun U.A., Breda (NL)

(72) Inventors: Robert Lazeroms, Sprundel (NL); Harry Raaijmakers, Roosendaal (NL); Cornelis Eme Koning, Zwolle (NL); Alwin Papegaaij, Kampen (NL); Antonia Urmanova, Zwolle (NL)

(73) Assignee: Coöperatie Koninklijke Cosun U.A., Breda (NL)

( * ) Notice: Subject to any disclaimer, the term of this patent is extended or adjusted under 35 U.S.C. 154(b) by 0 days.

(21) Appl. No.: 16/342,215

(22) PCT Filed: Oct. 19, 2017

(86) PCT No.: PCT/NL2017/050685
§ 371 (c)(1),
(2) Date: Apr. 16, 2019

(87) PCT Pub. No.: WO2018/074926
PCT Pub. Date: Apr. 26, 2018

(65) Prior Publication Data
US 2019/0284201 A1    Sep. 19, 2019

(30) Foreign Application Priority Data

Oct. 19, 2016 (EP) .................................. 16194629

(51) Int. Cl.
*C07D 493/04* (2006.01)
*C07D 317/22* (2006.01)
*C07D 407/04* (2006.01)
*C07D 407/14* (2006.01)
*C07H 9/04* (2006.01)
*C07H 13/10* (2006.01)
*C07H 13/12* (2006.01)

(52) U.S. Cl.
CPC ......... *C07D 493/04* (2013.01); *C07D 317/22* (2013.01); *C07D 407/04* (2013.01); *C07D 407/14* (2013.01); *C07H 9/04* (2013.01); *C07H 13/10* (2013.01); *C07H 13/12* (2013.01)

(58) Field of Classification Search
CPC .. C07D 493/04; C07D 317/22; C07D 407/04; C07D 407/14; C07H 9/04; C07H 13/10; C07H 13/12
See application file for complete search history.

(56) References Cited

U.S. PATENT DOCUMENTS

2008/0300383 A1* 12/2008 Verdianz .................. B01J 20/26
530/334
2014/0073589 A1* 3/2014 Whomsley ........... A61K 47/549
514/25

FOREIGN PATENT DOCUMENTS

| WO | 2006000008 A1 | 1/2006 |
| WO | 2006091902 A2 | 8/2006 |
| WO | 2012127119 A2 | 9/2012 |
| WO | 2014002039 A1 | 1/2014 |

OTHER PUBLICATIONS

Slivkin et al., Deposited Doc. (1975), VINITI, 3260-75, 14 pp. Avail.: VIVITI (CAS Abstract) (Year: 1975).*
K. Butler et al: 144. The synthesis of some galactaric (mucic) acid derivatives, Journal of the Chemical Society, Jan. 1, 1958 (Jan. 1, 1958), p. 740, XP055323965, Letchworth; GB. ISSN: 0368-1769, DOI: 10.1039/jr9580000740. Compounds I, Id, Ie, Il; their syntheses in Experimental part;; p. 740, paragraph 1st.
Haworth W N et al: Simple Carbohydrates Containing Unsaturated Substituents, Journal of the Chemical Society, Chemical Society, Letchworth; GB, Jan. 1, 1946 (Jan. 1, 1946), pp. 488-491, XP009053096, ISSN: 0368-1769, DOI: 10.1039/JR9460000488. Compounds I, II, III, IV,VII and their preparation; p. 489; compounds I, II, III, IV,VII.
Scoccia J et al: unsaturated diesters of primary, secondary, and tertiary dials derived from dimethyl (+)-tartrate and galactaric acid, European Journal of Organic Chemistry, Wiley—V C H Verlag GMBH & Co. KGAA, DE, No. 20, Jan. 1, 2013 (Jan. 1, 2013), pp. 4418-4426, XP009192629, ISSN: 1434-193X. Scheme 3; p. 4420; compounds III, IV.
Database Caplus [Online]; Chemical Abstracts Service, Columbus, Ohio, US; 1975, Slivkin, A.I.: "Unsaturated hydroxy acid esters based on monosaccharides and their polymerization", XP002765284, Database accession No. 1978:136873; *the whole document*.

* cited by examiner

Primary Examiner — Timothy R Rozof
(74) Attorney, Agent, or Firm — N.V. Nederlandsch Octrooibureau; Catherine A. Shultz; Tamara C. Stegmann

(57) ABSTRACT

The present invention relates to new bi-functional and polyfunctional bis-dioxolanes and bis-dioxanes. The present inventors have established that the bis-dioxolanes and bis-dioxanes of the invention are highly advantageous as building blocks, cross-linking and/or coupling agents in polymer engineering. They can be derived from biomass sources in a highly efficient manner. The production of the present bis-dioxolanes and bis-dioxanes from biomass has the particular advantage that it facilitates the introduction of desired functionality in a highly flexible manner. Hence, the present invention provides novel bi- or polyfunctional bis-dioxolanes and bis-dioxanes, their production from renewable (biomass) sources, as well as their use in the engineering of polymers.

16 Claims, No Drawings

BIS-DIOX(OL)ANE COMPOUNDS

FIELD OF THE INVENTION

The present invention relates to new bi-functional and polyfunctional bis-diox(ol)ane compounds, to methods of preparing them and the uses thereof in the production and/or modification of polymers. The invention, more in particular concerns a new class of bi-functional and polyfunctional bis-diox(ol)ane compounds that can be derived from biomass in a manner that enables the introduction of functional groups with high versatility. The presence of two diox(ol) ane moieties in the basic structure of the molecules confers many interesting and highly distinctive properties to the polymer based materials they are incorporated in, e.g. to function as polymer cross-linker.

BACKGROUND OF THE INVENTION

In the field of polymer engineering there is an ever increasing interest in new approaches for producing polymer materials with specific and unique (combinations of) properties, such as enhanced thermal stability, multiphase physical responses, compatibility, impact response, flexibility, and rigidity. One of the recent directions regarding polymer modification is intended to reduce the environmental impact, in particular to improve biodegradability and/or to increase the biobased content.

One obvious way is to produce new polymers using new combinations of existing building blocks or employing specifically developed new biobased building blocks to bring specific properties to the resulting polymer material.

An attractive alternative to the development of new polymers, is the chemical modification of existing polymers. Surface and bulk properties can be improved easily by modifying conventional polymers. Materials produced using such techniques have attracted considerable attention in the industrial field as they can combine a variety of highly distinctive properties. Sometimes, balancing of properties is needed, and this is possible only through modification of polymers. Prime techniques for polymer modifications are grafting, crosslinking, blending, and composite formation.

As will be apparent for those skilled in the art, many modalities for development of new polymers and the modification of known ones depend on the availability of suitable bi- or polyfunctional monomers, which are capable of being incorporated in polymer chains and/or of forming 'bridges' within and/or among polymer chains under appropriate conditions. Although the suitability of these monomers for a given purpose primarily depends on the presence of functional groups capable of interacting with reactive groups present in the polymer chains of interest, the structure of the hydrocarbon backbone of the bi- and polyfunctional monomer equally affects important properties. One such property is the compatibility of the monomer with aqueous solvents and/or the ability to be reacted in an aqueous solvent. The interest in polymer systems that can be produced and/or processed in aqueous solvents has rapidly increased over the past decades, as environmental concerns have increased resistance to processes involving the use of (large quantities of) organic solvents. Moreover, for certain applications the use of aqueous solvent systems may be the preferred option simply for technical/chemical reasons.

The synthesis of bi- and polyfunctional monomers is challenging given the reactive nature of the functional groups that need to be incorporated and usually. Ideally 'platforms' are developed that make a variety of homofunctional and/or heterofunctional monomers accessible in a practical and cost-effective manner. Naturally, environmental considerations not only play a role in the production and/or processing of polymer systems, but equally so in the production of the monomers as starting materials. Ideally, bi- and polyfunctional monomers are developed that are based on renewable sources rather than on petrochemicals.

Presently known techniques at best constitute a compromise meeting some of these demands and often only to a limited extent. Hence, there is a strong interest in new, preferably biobased, bi- or polyfunctional compounds that have utility in the development of new polymer based materials and there is accordingly a desire for new approaches for their production in an economically feasible and flexible manner.

The present invention seeks to provide solutions to any or all of the aforementioned objectives.

SUMMARY OF THE INVENTION

According to the present invention, this objective is met with certain bi-functional or poly-functional bis-dioxolane and bis-dioxane compounds having a general structure represented by the following formulas (Ia) or I(b):

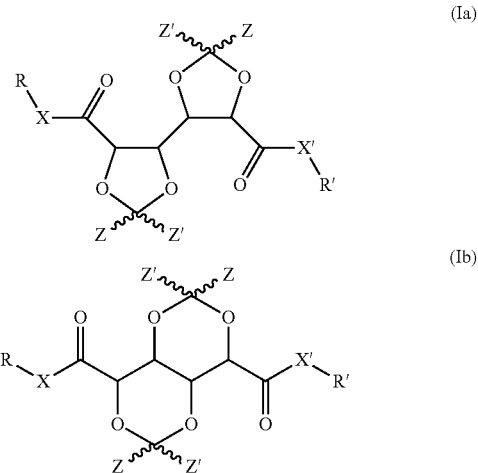

Bis-dioxolanes and bis-dioxanes according to formulas (Ia) and (Ib) can be derived from biomass sources in a highly efficient manner. The production of these bis-dioxolanes and bis-dioxanes from biomass according to the invention has the particular advantage that it facilitates the introduction of desired functionality in a highly flexible manner.

The present inventors have established that the bis-dioxolanes and bis-dioxanes represented by formulas (Ia) and (Ib) can advantageously be used as biobased building blocks, cross-linking and/or coupling agents in polymer engineering, to confer highly interesting and distinctive properties. It has been found that compounds according to the invention generally have good water-solubility, in particular when compared to corresponding structures derived from petrochemical sources. For instance, a bis-dioxolane equivalent of the known β-hydroxyalkyl-amide cross-linker available under the tradename Primid® has significantly higher water solubility, which opens up an array of new applications.

The molecules of the invention are characterized by a high oxygen content and relative rigidity of the basic structure owing to the presence of the two cyclic acetal moieties.

The present bi- or polyfunctional bis-dioxolanes and bis-dioxanes, to the best knowledge of the inventors, have never been disclosed in the art before.

WO2006/091902 discloses the conversion of aldaric acids into certain bifunctional amide derivatives, which are said to have utility as a monomer or polymer cross-linker. The same or a very similar concept is discussed in WO2012/127119. This document also discloses the use of the resulting aldaric acid (di)allylamide derivatives for cross-linking functionalized polysaccharides to produce hydrogels.

Hence, the present invention provides novel bi- or polyfunctional bis-dioxolanes and bis-dioxanes, their production from renewable (biomass) sources, as well as their use in the engineering of polymers. These and other aspects will be described and illustrated in more detail here below.

DETAILED DESCRIPTION

A first aspect of the invention concerns bis-dioxolanes and bis-dioxanes having a structure represented by formula (Ia) or (Ib):

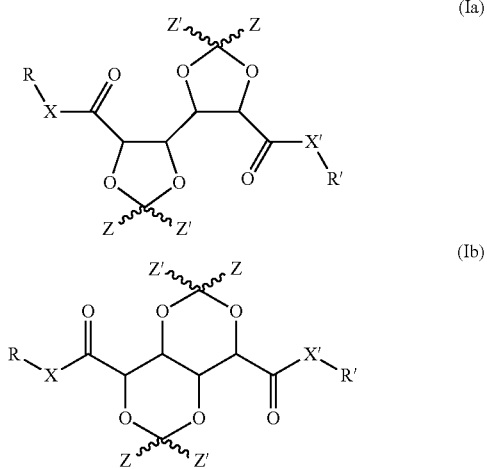

wherein
X represents a heteroatom or heteroatom containing group independently selected from —O—, —NH— and —NR$^a$—;
X' represents a heteroatom or heteroatom containing group independently selected from —O—, —NH— and —NR$^{a'}$—;
Z and Z' independently represent hydrogen, a straight chain or branched $C_1$-$C_4$alkyl or benzyl or the moiety Z—C—Z' represents a 5-, 6-, or 7-membered cyclic or heterocyclic group; and
R, R', R$^a$ and R$^{a'}$ independently represent a reactive group containing moiety represented by the formula —($C_1$-$C_8$alkyl)-Q, wherein Q represents a functional group and —$C_{1-8}$alkyl represents a branched or straight chain aliphatic alkyl group comprising 1 to 8 carbon atoms.

The terms 'bis-dioxolane' and 'bis-dioxane' is used herein to denote the compounds of the invention, because of the characteristic structural feature common to all compounds of the invention, notably the presence of two neighbouring 1,3-dioxolane moieties or two fused 1,3-dioxane moieties respectively, which may be (further) substituted. Furthermore, the terms 'bifunctional' and 'polyfunctional' are used herein to indicate that the compounds comprise two or more than two functional groups, more in particular two or more than two reactive groups, respectively. As will be evident from the definition above, the compounds contain at least two such functional groups at the positions represented by R and R' in the structure of formulas (Ia) and (Ib) and additional functional groups may be present if X and/or X' represents —NR$^a$— and —NR$^{a'}$— respectively. Hence the consistent reference in this document to bi-functional as well as polyfunctional bis-dioxolanes and bis-dioxanes. For ease of reference, the compounds of the present invention, may also collectively be referred to herein as the 'bifunctional or polyfunctional bis-diox(ol)anes' or simply as the 'bis-diox(ol)anes'.

As will be recognized by those skilled in the art, based on the definition of formulas (Ia) and (Ib) herein, it is envisaged that bis-dioxolanes and bis-dioxanes can be provided comprising different heteroatoms and/or different functional groups at the respective positions within the structure. In certain embodiments of the invention, the bis-dioxolane and bis-dioxane compounds have symmetrical structures, Hence in certain embodiments of the invention compounds as defined herein are provided, wherein X and X' are the same. Furthermore, in certain embodiments of the invention compounds as defined herein are provided, wherein R, R', R$^a$ and R$^{a'}$ are the same. In certain embodiments X and X' are the same and R, R', R$^a$ and R$^{a'}$ are the same.

In certain embodiments of the invention, X and X' in formulas (Ia) and (Ib) as defined herein represent —O— or —NH—, preferably they represent —NH—.

Furthermore, in certain embodiments of the invention Z, in the above formulas (Ia) and (Ib), represents methyl.

In certain embodiments of the invention, Z and Z' in formulas (Ia) and (Ib) as defined herein independently represent hydrogen straight chain or branched $C_1$-$C_4$alkyl or benzyl. In a preferred embodiment Z and Z' independently represent hydrogen, methyl, ethyl, propyl, butyl, more preferably hydrogen, methyl or ethyl. In a particularly preferred embodiment of the invention Z and Z' are the same. Most preferably Z and Z' are the same and both represent hydrogen, methyl or ethyl, most preferably methyl. In some embodiments of the invention, the moiety Z—C—Z' represents a 5-, 6-, or 7-membered, preferably a 6-membered, cyclic or heterocyclic group, which may be saturated or unsaturated. In embodiments wherein said moiety represents a heterocyclic group, it typically comprises one or more ring oxygen atoms, preferably one ring oxygen atom. In some embodiments of the invention, the moiety Z—C—Z' represents cyclohexyl.

As will be understood by those skilled in the art, the groups represented by R, R', R$^a$ and R$^{a'}$ in formulas (Ia) and (Ib) as defined herein comprise a functional group, represented by Q, as well as a bridging aliphatic alkyl group comprising 1 to 8 carbon atoms, which may be branched or straight chain, denoted '—($C_1$-$C_8$alkyl)-'.

The term 'functional group', in the field of polymer engineering, is generally understood to refer to a chemical moiety that is capable of interacting with another group to form, typically, a covalent or ionic bond. In preferred embodiments of the invention Q, in the above definition of formulas (Ia) and (Ib), represents a reactive group. The term "reactive group" as used herein refers to a group that is capable of reacting with another chemical group to form a covalent bond, i.e. is covalently reactive under suitable reaction conditions, and generally represents a point of attachment for another substance. Reactive groups generally include nucleophiles, electrophiles and photoactivatable groups. In preferred embodiments of the invention Q, in the above definition of formulas (Ia) and (Ib), represents a reactive group selected from amine, thiol, carboxyl, oxy, ethenyl, ethynyl, nitril, cyanate, isocyanate, thiocyanate, isothiocyanate, imine, imide, azide, nitrile, nitrite, nitro, nitroso, epoxide, cyclic carbonate, oxazoline, anhydride, acrylate and chlorotriazine. In preferred embodiments of the invention Q, in the above definition of formulas (Ia) and (Ib), represents a reactive group selected from the group consisting of epoxide and ethenyl.

In other preferred embodiments of the invention Q, in the above definition of formulas (Ia) and (Ib), represents a reactive group selected from hydroxyl, amine, thiol, carboxyl, oxy, ethenyl, ethynyl, nitril, cyanate, isocyanate, thiocyanate, isothiocyanate, imine, imide, azide, nitrile, nitrite, nitro, nitroso, epoxide, cyclic carbonate, oxazoline, anhydride, acrylate and chlorotriazine.

In other preferred embodiments of the invention Q, in the above definition of formulas (Ia) and (Ib), represents a reactive group selected from hydroxyl, amine, thiol, carboxyl, oxy, ethynyl, nitril, cyanate, isocyanate, thiocyanate, isothiocyanate, imine, imide, azide, nitrile, nitrite, nitro, nitroso, epoxide, cyclic carbonate, oxazoline, anhydride, acrylate and chlorotriazine.

In preferred embodiments of the invention Q in the above definition of formulas (Ia) and (Ib), represents a reactive group selected from hydroxyl, amine, thiol, carboxyl, oxy, cyanate, isocyanate, imine, imide, and oxazoline.

In preferred embodiments of the invention Q in the above definition of formulas (Ia) and (Ib), represents a reactive group selected from hydroxyl, amine, thiol, carboxyl, oxy, cyanate, isocyanate, imine, imide, and oxazoline, most preferably hydroxyl.

The branched or straight chain aliphatic alkyl groups that are part of the moieties represented by R, R', $R^a$ and $R^{a'}$ can typically comprise up to 8 carbon atoms. For the avoidance of doubt, it is to be noted that the indicated number of carbon atoms concerns the total number of carbon atoms, i.e. it includes any carbon atom that is not part of the main chain connecting X and Q in the above formulas (Ia) and (Ib). In a preferred embodiment, the alkyl groups are saturated. Furthermore, in a preferred embodiment, the alkyl groups do not comprise any heteroatoms and/or non-alkyl substituents. In certain preferred embodiments, the aliphatic alkyl groups that are part of the moieties represented by R, R', $R^a$ and $R^{a'}$ comprises 1 to 6 carbon atoms, more preferably 1 to 4 carbon atoms or 1 to 2 carbons atoms. In embodiments of the invention R, R', $R^a$ and $R^{a'}$, in the above formulas (Ia) and (Ib), independently represent a reactive group containing moiety represented by the formula —($C_1$-$C_6$alkyl)-Q, preferably by the formula —($C_1$-$C_4$alkyl)-Q, more preferably by the formula —($C_1$-$C_2$alkyl)-Q. In certain preferred embodiments of the invention the branched or straight chain aliphatic alkyl group that are part of the moieties represented by R, R', $R^a$ and $R^{a'}$ are selected from the group consisting methylene, ethylene, propylene, isopropylene and butylene.

In a preferred embodiment of the invention bis-dioxolanes and bis-dioxanes having a structure represented by formula (Ia) or (Ib) are provided, wherein X represents a heteroatom or heteroatom containing group independently selected from —O—, —NH— and —$NR^a$—; X' represents a heteroatom or heteroatom containing group independently selected from —O—, —NH— and —$NR^{a'}$—; Z and Z' independently represent hydrogen, a straight chain or branched $C_1$-$C_4$alkyl; and R, R', $R^a$ and $R^{a'}$ independently represent a reactive group containing moiety represented by the formula —($C_1$-$C_6$alkyl)-Q, wherein —$C_{1-6}$alkyl represents a branched or straight chain aliphatic alkyl group comprising 1 to 6 carbon atoms, and Q represents a reactive group selected from hydroxyl, amine, thiol, carboxyl, oxy, cyanate, isocyanate, thiocyanate, isothiocyanate, imine, imide, epoxide, cyclic carbonate, oxazoline, anhydride and acrylate.

In a particularly preferred embodiment of the invention bis-dioxolanes and bis-dioxanes having a structure represented by formula (Ia) or (Ib) are provided, wherein: X represents a heteroatom or heteroatom containing group independently selected from —O—, —NH— and —$NR^a$—; X' represents a heteroatom or heteroatom containing group independently selected from —O—, —NH— and —$NR^{a'}$—; Z and Z' independently represent hydrogen, a straight chain or branched $C_1$-$C_2$alkyl; and R, R', $R^a$ and $R^{a'}$ independently represent a reactive group containing moiety represented by the formula —($C_1$-$C_4$alkyl)-Q, wherein —$C_{1-4}$alkyl represents a branched or straight chain aliphatic alkyl group comprising 1 to 4 carbon atoms, and Q represents a reactive group selected from hydroxyl, amine, thiol, carboxyl, oxy, cyanate, isocyanate, imine, imide, and oxazoline.

As will be evident to those of average skill in the art, the present bis-dioxolanes and bis-dioxanes comprise numerous centers of chirality. The invention is not particularly limited with regard to the orientation of these chiral centers. Nonetheless, in accordance with the invention, it is particularly preferred to produce the present bis-dioxolanes and bis-dioxanes from biomass sources, as is explained in more detail herein elsewhere, and there is a particular configuration that is inherent to such compounds as obtained from biomass sources.

Hence, in preferred embodiments of the invention, a bis-dioxolane as defined herein is provided, having the structure represented by formula (IIa):

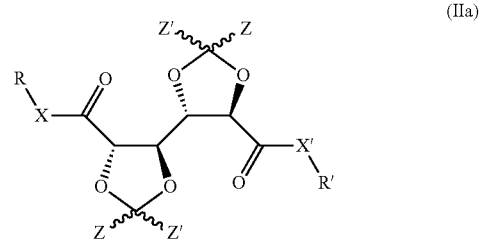

(IIa)

wherein R, R', X, X' and Z all have the same meaning as defined herein elsewhere in relation to formula (Ia).

In other embodiments of the invention, a bis-dioxane as defined herein is provided, having the structure represented by formula (IIb) or (IIc):

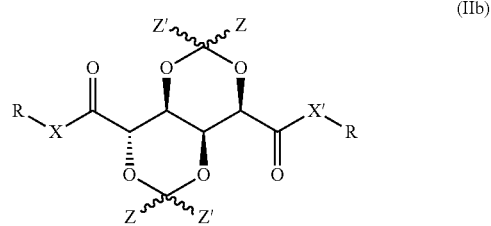

(IIb)

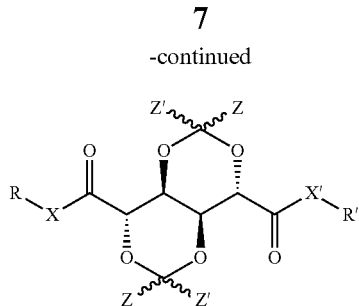

(IIc)

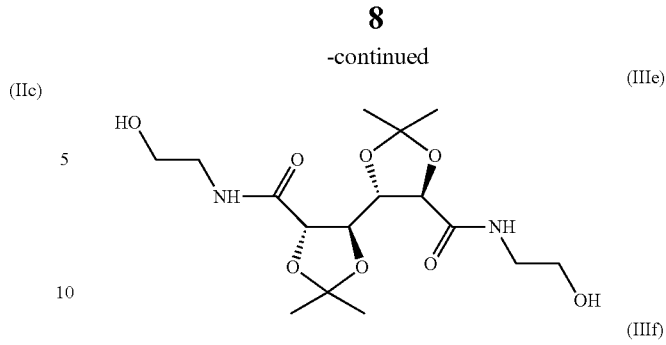

(IIIe)

wherein R, R', X, X' and Z all have the same meaning as defined herein elsewhere in relation to formula (Ib).

In certain embodiments of the invention, bis-dioxolanes are provided having the structure represented by any of formulas (IIIa)-(IIIh) as depicted below. The bis-dioxolanes having the structure represented by formulas (IIIb), (IIId), (IIIe), (IIIf), (IIIg) and (IIIh) represent particularly preferred examples of the present invention, of which the bis-dioxolanes having the structure represented by formulas (IIIe), (IIIf) and (IIIg) stand out in particular.

(IIIa)

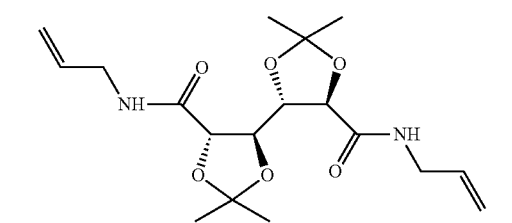

(IIIf)

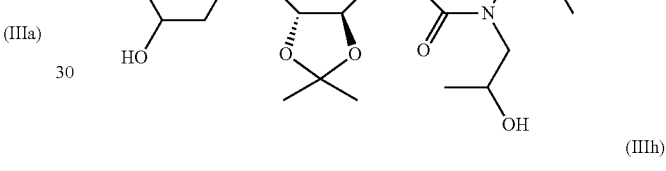

(IIIg)

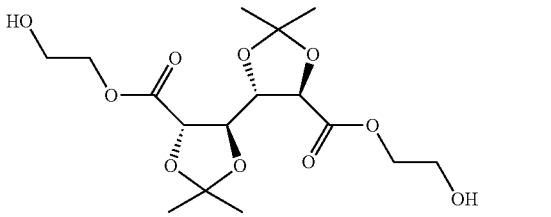

(IIIb)

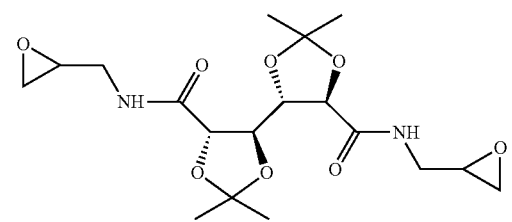

(IIIh)

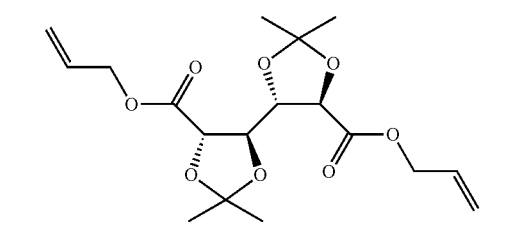

(IIIc)

A second aspect of the invention, concerns a method of producing a bis-dioxolane or bis-dioxane as defined herein, said method comprising the steps of
a) providing a source of a C6 aldaric acid;
b) derivatization of the C6 aldaric acid by combining the source of the C6 aldaric acid with a lower alkyl alcohol under conditions that cause the lower alkyl alcohol to react with the C6 aldaric acid carboxyl groups to form lower alkyl ester moieties;
c) acetalisation of the esterified C6 aldaric acid as obtained in step b) by combining it with an acetalisation reagent, selected from the group of compounds having the formula Z—C(=O)—Z', wherein Z and Z' have the same meaning as defined in relation to formulas (Ia) and (Ib), and the corresponding di-alkoxyacetals and di-alkoxyketals, under conditions that cause the acetalisation reagent to react with the aldaric acid hydroxyl groups to form the corresponding bis-diox(ol)anes;
d) conversion of the bis-diox(ol)anes obtained in step c) by reaction with a hydroxyl or amine reagent, selected from the group consisting of Q-($C_1$-$C_8$alkyl)-OH; Q-($C_1$-$C_8$alkyl)-$NH_2$ and Q-($C_1$-$C_8$alkyl)-NH—($C_1$-$C_8$alkyl)-Q, wherein Q and $C_1$-$C_8$alkyl have the same meaning as defined in relation to formulas (Ia) and (Ib), under conditions that cause the (IIId)

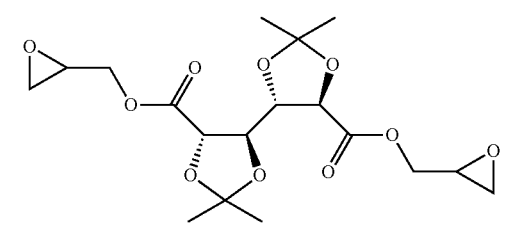

hydroxyl or amine reagent to displace the lower alkyl groups of the ester moieties of the bis-diox(ol)anes to form a bi-functional or polyfunctional bis-diox(ol)ane of the invention.

As will be understood by those skilled in the art, in accordance with the invention it is preferred that starting compound for the process of the invention is derived from a biomass source. For that reason, it is particularly preferred that the C6 aldaric acid is galactaric acid. Embodiments are however also envisaged wherein the C6 aldaric acid is mannaric acid or glucaric acid. The present inventors have observed that the use of galactaric acid as the starting compound in the processes of the invention yields the corresponding bis-dioxolane, i.e. the 2,3;4,5-diacetal, as defined herein, whereas the use of mannaric acid or glucaric acid yields the corresponding bis-dioxane, i.e. the 2,4;3,5-diacetal, as defined herein. Without wishing to be bound by any theory, the inventors believe that one form is energetically highly favoured over the other.

In the context of the present invention, a 'source of C6 aldaric acid' can be any composition containing substantial amounts of the C6 aldaric acid, typically as the major component. In embodiments of the invention, the source of C6 aldaric acid comprises more than 90 wt. %, based on dry solids weight, of C6 aldaric acid, more preferably more than 95 wt. %, more than 96 wt. %, more than 97 wt. %, more than 98 wt. %, more than 99 wt. % of C6 aldaric acid. In some embodiments the source of C6 aldaric acid comprises substantially or completely pure C6 aldaric acid. In some embodiments of the invention, step a) comprises providing a solution of C6 aldaric acid in a solvent in which the derivatization according to step b) can conveniently be carried out.

As already explained herein, it is particularly preferred in accordance with the invention that the bis-diox(ol)ane compounds are produced from a renewable source, in particular from a biomass source.

In accordance with one embodiment, suitable biomass sources include those containing substantial quantities of galacturonic acid, such as hemicellulosic and pectin rich biomass. Materials may accordingly be utilized that, at present, are still mainly considered by-products in various industries. Turning such by-products into a new natural resource, is obviously an advantage. In preferred embodiments of the invention, the hemicellulose and pectin rich biomass is sugar beet pulp, which constitutes the production residuum from the sugar beet industry. The production of galactaric acid from hemicellulose and pectin rich biomass involves the extraction of galacturonic acid and subsequent conversion of galacturonic acid into galactaric acid by selective oxidation of the terminal hydroxyl group. A highly efficient process for the oxidative conversion of galacturonic acid to galactaric acid, has recently been disclosed in international patent applications WO 2013/151428 and WO 2016/056907, the contents of which are incorporated herein by reference.

As indicated herein, step b) comprises combining the source of the C6 aldaric acid with a lower alkyl alcohol under conditions that cause the alcohol to react with the C6 aldaric acid carboxyl groups to form lower alkyl ester moieties.

Suitable examples of lower alkyl alcohols include methanol, ethanol, propanol and isopropanol. Methanol and ethanol are preferred. Most preferably, the lower alkyl alcohol is ethanol.

In accordance with preferred embodiments of the present invention, step b) is carried out in the presence of a suitable catalyst. Suitable catalysts include acid The use of sulfuric acid is particularly preferred.

Examples of suitable solvents for carrying out step b) include alcohols. The use of ethanol is particularly preferred.

It is within the routine of those of average skill in the art to determine the appropriate conditions for carrying out the process and to optimize it in terms of yield, efficiency, etc.

As indicated herein, step c) comprises combining the esterified aldaric acid obtained in step b) with an acetalisation reagent under conditions that cause the acetalisation reagent to react with the aldaric acid hydroxyl groups to form the corresponding bis-diox(ol)ane.

The acetalisation reagent is an aldehyde or a ketone containing lower alkyl compound having the formula Z—C(=O)—Z', with Z and Z' being as defined in relation to formulas (Ia) and (Ib) above. It is also feasible to use the corresponding di-alkoxyacetals and di-alkoxyketals, where the oxo group of the aldehyde or ketone has been converted into a di-alkoxy moiety. Typically these di-alkoxyacetals and di-alkoxyketals have the general formula Z—C(OR$^b$OR$^{b'}$)—Z', with Z and Z' being as defined in relation to formulas (Ia) and (Ib) and R$^b$ and R$^{b'}$ representing lower alkyl, typically methyl or ethyl, most preferably methyl.

In a particularly preferred embodiment of the invention, the acetalisation reagent is selected from the group consisting of formaldehyde, acetaldehyde, acetone, propanal, butanone, butanal, cyclohexanone, benzaldehyde and the corresponding dialkoxylated, preferably dimethoxylated, acetals or ketals thereof. Most preferably the acetalisation reagent is 2,2-dimethoxypropane.

The acetalisation is typically carried out in the presence of a suitable catalyst. Suitable catalysts include acid The use of p-toluene-sulfonic acid is particularly preferred.

Suitable solvents include. Acetone, methylene chloride The use of methylene chloride is particularly preferred.

It is within the routine of those of average skill in the art to determine the appropriate conditions for carrying out the process and to optimize it in terms of yield, efficiency, etc. Additionally, processes of producing bis-diox(ol)ane compounds from aldaric acids have been described in the art. For illustrative purposes, Prömper et al. (Green Chem, 2006, 8, 467-478) and Munoz-Guerra et al. (Green Chem, 2014, 16, 1716-1739) may be referred to in this regard.

As indicated herein, step d) comprises reacting the bis-diox(ol)ane as obtained in step c) with a hydroxyl or amine reagent under conditions that cause the hydroxyl or amine containing reactant to displace the lower alkyl groups of the ester moieties of the bis-diox(ol)anes to form the bi-functional or polyfunctional bis-diox(ol)ane compounds of the invention.

The hydroxyl or amine reagent is typically selected from the group consisting of Q-($C_1$-$C_8$alkyl)-OH; Q-($C_1$-$C_8$alkyl)-NH$_2$ and Q-($C_1$-$C_8$alkyl)-NH—($C_1$-$C_8$alkyl)-Q, wherein Q and $C_1$-$C_8$ alkyl have the same meaning as defined in relation to formula (I). As will be understood by those of ordinary skill in the art, the precise structure of the hydroxyl or amine reagent depends mainly on the functional group(s) that are desired in the bi- or polyfunctional bis-diox(ol)ane. The bis-diox(ol)ane compound as obtained in step c) of the present process can be reacted with a very wide variety of hydroxyl and amine containing reactants according to this invention, with invariably high efficiency and selectivity, which constitutes one of the significant advantages of the present invention.

The reaction is typically carried out by combining the bis-diox(ol)ane as obtained in step c) with the hydroxyl or amine containing reactant in a suitable solvent and applying conditions under which the displacement occurs. In case the target product is the allyl ester, the displacement reaction involves an equilibrium between the starting lower alkyl esters and the target derivative. This equilibrium can be driven towards the target compound by using an excess amount of the alcohol. In case the target product is the allyl amide derivative, this target product is in fact the energetically favoured product.

Hence, in certain embodiments of the invention processes as defined herein are provided for producing a compound according to formulas (Ia) and (Ib) wherein X and X' represent —O— and step d) comprises:

d1) combining the bis-diox(ol)ane with a stoichiometric excess of a hydroxyl containing reactant having the formula $Q\text{-}(C_1\text{-}C_8\text{alkyl})\text{-OH}$, optionally in a suitable solvent, to produce a liquid reaction mixture;

d2) subjecting the liquid reaction mixture to conditions under which the displacement reaction proceeds.

Suitable solvents include C1-C8 alcohols containing the required functional end groups, C1-C4 containing the required functional end groups The use of allyl alcohol is particularly preferred.

The transesterification reaction is typically carried out by contacting the bis-diox(ol)ane product with an excess of one of the above mentioned alcohols in the presence of a suitable alkaline catalyst. Suitable alkaline catalysts include sodium alkoxide, sodium hydroxide, sodium carbonate, strong alkaline resins The use of sodium methoxide is particularly preferred.

The molar ratio of the hydroxyl containing reactant to the bis-diox(ol)ane is typically in excess of the stoichiometric ratio. In particular, the molar ratio of the hydroxyl containing reactant to the bis-diox(ol)ane may be in the range of 3 to 100, preferably 5 to 80, more preferably 10 to 60.

It is within the routine of those of average skill in the art to determine the appropriate conditions for carrying out the process and to optimize it in terms of yield, efficiency, etc.

The process may conveniently be carried out in a batch reactor, such as a continuous stirred tank reactor (CSTR). The reaction is typically carried out at a temperature and pressure and for a contact time sufficient to effect the formation of the target ester derivative. In certain embodiments of the invention, the reaction is carried out under reflux conditions. In certain embodiments of the invention, step d2) comprises subjecting the liquid reaction mixture to temperatures within the range of 20° C. to 120° C., preferably within the range of 30 to 100° C., preferably within the range of 40-90° C., more preferably within the range of 50-85° C., and most preferably within the range of 60-80° C. In certain embodiments of the invention, step d2) comprises subjecting the liquid reaction mixture to a pressure within the range of 0.01-10 Bar, preferably within the range of 0.05-5 Bar, more preferably within the range of 0.05-3 Bar The reaction is carried for a period of time sufficient to effect conversion under the chosen conditions. The reaction time can typically range from several hours to a number of days, typically from 3 hours to 125 hours, most preferably from 10-100 hours. Conversion of the bis-diox(ol)ane into the target compound is preferably from about 20% to about 100% and most preferably from about 60% to about 100%. Selectivity for the target bis-diox(ol)ane, is preferably from about 20% to 100% and most preferably from about 60% to 100%.

Alternatively, in certain embodiments of the invention processes as defined herein are provided for producing bis-diox(ol)anes according to formulas (Ia) and (Ib) wherein X and X' represent —NH—, —NR$^a$— or —NR$^{a'}$—, and step d) comprises: d1') combining the bis-diox(ol)ane with stoichiometric excess of the amine containing reactant selected from the group consisting of $Q\text{-}(C_1\text{-}C_8\text{alkyl})\text{-NH}_2$ and $Q\text{-}(C_1\text{-}C_8\text{alkyl})\text{-NH}\text{—}(C_1\text{-}C_8\text{alkyl})\text{-Q}$ in a suitable solvent, to produce a liquid reaction mixture; d2') subjecting the liquid reaction mixture to conditions under which the displacement reaction proceeds.

Suitable solvents according to these embodiments include methanol and ethanol. The use of ethanol is particularly preferred.

The molar ratio of the amine containing reactant to the bis-diox(ol)ane is typically in slight excess of the stoichiometric ratio. In preferred embodiments, the molar ratio of the amine containing reactant to the bis-diox(ol)ane may be in the range of 2.01-10, preferably 2.05-5, more preferably 2.1-2.5.

Step d1') and d2') may conveniently be carried out in a batch reactor, such as a CSTR. The reaction is typically carried out at a temperature and pressure and for a contact time sufficient to effect the formation of the ester/amide moieties. In certain embodiments of the invention, the reaction is carried out under reflux conditions. In certain embodiments of the invention, step d2') comprises subjecting the liquid reaction mixture to temperatures within the range of 20° C. to 120° C., preferably within the range of 20 to 100° C., preferably within the range of 20-90° C., more preferably within the range of 20-85° C., and most preferably within the range of 20-80° C. In certain embodiments of the invention, step d2') comprises subjecting the liquid reaction mixture to a pressure within the range of 0.01-10 Bar, preferably within the range of 0.05-5 Bar, more preferably within the range of 0.05-3 Bar The reaction is carried out for a period of time sufficient to effect conversion under the chosen conditions. The reaction time can range from several minutes to a number of days, typically from 30 minutes to 50 hours, most preferably from 3-24 hours. Conversion of the bis-diox(ol)ane into the target compound is preferably from about 20% to about 100% and most preferably from about 60% to about 100%. Selectivity for the target bis-diox(ol)ane, is preferably from about 20% to 100% and most preferably from about 60% to 100%.

In certain embodiments of the invention, step d2) or d2') may be followed by a step d3) comprising the separation and/or isolation of the bis-diox(ol)ane from the reaction mixture, by any suitable technique known by the person skilled in the art, such as chromatographic separation and/or crystallization. Embodiments are also envisaged, wherein the reaction mixture produced in step d2) is immediately used for further conversion reactions, e.g. additional displacement reactions, as will be illustrated in the examples, wherein allyl esters and allyl amides according to formulas (Ia) and (Ib) are converted to epoxy esters and epoxy amides according to formulas (Ia) and (Ib) respectively. For instance, the allyl ester of formula (IIIa) can be converted to the epoxy ester of formula (IIIb) and the allyl amide of formula (IIIc) can be converted to the epoxy amide of formula (IIId).

Alternatively, the epoxy esters according to formulas (Ia) and (Ib) can be produced by first converting an aldaric acid into the corresponding di-carboxylic bis-diox(ol)ane and subsequently reacting said di-carboxylic bis-diox(ol)ane with epichlorohydrin, which is preferably a biobased.

A further aspect of the invention, concerns compounds and composition as obtained and/or obtainable by the methods defined herein. Such compounds and/or compositions may be the same or may differ in some aspect(s) from compounds and/or compositions as described herein.

A further aspect of the invention concerns the use of the bi- or polyfunctional bis-diox(ol)ane as defined herein and/or as obtainable by the methods as defined herein for the production and/or modification of polymer materials. In a particularly preferred embodiment of the invention, said use involves production and/or modification processes that are performed in an aqueous solvent.

In an embodiment of the invention, the use of the bi- or polyfunctional bis-diox(ol)ane as defined herein and/or as obtainable by the methods as defined herein is provided as a polymer cross-linking and/or for cross-linking polymers. In a particularly preferred embodiment of the invention, said use involves the cross-linking of polymers in an aqueous solvent.

In an embodiment of the invention, the use of the bi- or polyfunctional bis-diox(ol)ane as defined herein and/or as obtainable by the methods as defined herein is provided as a coupling agent in polymer composite materials and/or for producing and/or modifying polymer composite materials. In a particularly preferred embodiment of the invention, said use involves the coupling and/or production and/or modification of polymer composites in an aqueous solvent.

In an embodiment of the invention, the use of the bi- or polyfunctional bis-diox(ol)ane as defined herein and/or as obtainable by the methods as defined herein is provided as a polymer building block and/or for building polymers.

The types of polymers that can be produced and/or modified using the bi- or polyfunction dioxolane compounds of the invention is virtually limitless as a large variety of functional groups can be incorporated. To name just a few exemplary materials wherein the present bi- of polyfunction bis-diox(ol)anes have particular utility, polyesters, polyurethanes and polycarbonates.

The present invention has been described above with reference to a number of exemplary embodiments as shown in the drawings. Modifications and alternative implementations of some parts or elements are possible, and are included in the scope of protection as defined in the appended claims.

EXAMPLES

Example 1: Synthesis of GalX-allylester

Sodium methoxide (0.16 g, 2.9 mmol) was added to a solution of GalX (20.0 gram, 57.8 mmol, obtained following procedures described in literature, allyl alcohol (250 mL). The solution was refluxed for 5 days. After cooling down and evaporation, the solid material was stirred in heptane and filtrated to remove the salts. The product was isolated after evaporation of heptanes, followed by crystallization from ethanol and water, filtrated and dried in a vacuum oven.

Product GalX-allylester (Mw 370): 15.4 gram (yield 72%). HPLC: 99% pure material. $^1$H NMR (400.17 MHz, CDCl$_3$): δ (ppm)=5.92 (m, 2H); 5.36 (dd, $^2J_{HH}$=17.2 Hz, $^3J_{HH}$=1.4 Hz, 2H); 5.27 (dd, $^2J_{HH}$=10.4 Hz, $^3J_{HH}$=1.2 Hz, 2H); 4.69 (d, $^3J_{HH}$=5.85 Hz, 4H); 4.62 (dd, $^2J_{HH}$=4.3 Hz, $^3J_{HH}$=1.3 Hz, 2H); 4.49 (dd, $^2J_{HH}$=4.2 Hz, $^3J_{HH}$=1.3 Hz, 2H); 1.49 (s, 6H); 1.44 (s, 6H). $^{13}$C NMR (100.62 MHz, CDCl$_3$): δ (ppm)=170.74 (C=O); 131.45 (CH$_2$=CH); 119.30 (CH$_2$=CH); 112.53 (C(CH$_3$)$_2$); 79.28 (CHCH); 76.13 (C=OCHCH); 66.22 (CH$_2$OC=O); 27.15 (CCH$_3$); 26.12 (CCH$_3$).

| eq | Compound | Mw (g/mol) | Density (g/ml) | Quantity (g) | Quantity (ml) | Quantity (mmol) |
|---|---|---|---|---|---|---|
| 1 | GalX | 346 | — | 20.0 | — | 57.8 |
|  | Allylalcohol | 58.1 | 0.854 | — | 250 | — |
| 0.2 | Sodium methoxide (NaOMe) | 54.0 | — | 0.63 | — | 11.6 |
| 1 | GalX-allylester | 370 | — | 21.4 | — | 57.8 |

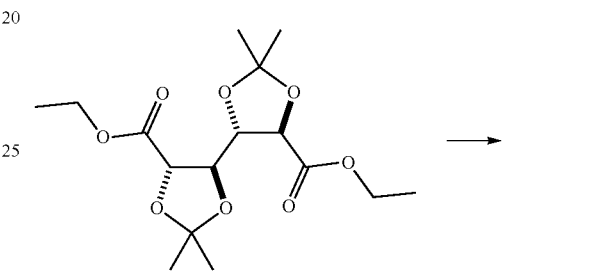

Chemical Formula: C$_{16}$H$_{26}$O$_8$
Molecular Weight: 346.38

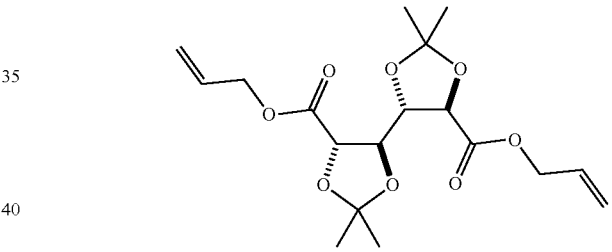

Chemical Formula: C$_{18}$H$_{26}$O$_8$
Molecular Weight: 370.40

Example 2: Synthesis of GalX-diepoxyester mCPBA (35.8 g, 208 mmol) was added to a solution of GalXallylester (11 gram, 29.7 mmol) in DCM (250 mL). The solution was stirred for 60 hours at reflux temperature. After cooling down, the solution was filtrated. The filtrate was washed with Na$_2$SO$_3$, Na$_2$CO$_3$ and water. The organic phase was evaporated to dryness. Product GalX-diepoxyester crude (Mw 402): 8.8 gram (yield 74%). HPLC: 99% pure material. $^1$H NMR (400.17 MHz, CDCl$_3$): δ (ppm)=4.61 (d, $^3J_{HH}$=4.4 Hz, 2H); 4.50 (dt, $^2J_{HH}$=12.2 Hz, $^3J_{HH}$=2.5 Hz, 2H); 4.46 (dd, $^2J_{HH}$=4.4 Hz, $^3J_{HH}$=1.3 Hz, 2H); 4.04 (ddd, $^2J_{HH}$=12.2 Hz, $^3J_{HH}$=6.2 Hz, $^4J_{HH}$=1.1 Hz, 2H); 3.20 (m, 2H); 2.81 (t, $^2J_{HH}$=4.8 Hz, 2H); 2.64 (dd, $^2J_{HH}$=4.9 Hz, $^3J_{HH}$=2.5 Hz, 2H); 1.47 (s, 6H); 1.42 (s, 6H). $^{13}$C NMR (100.62 MHz, CDCl$_3$): δ (ppm)=170.79 (C=O); 112.53 (C(CH$_3$)$_2$); 79.28 (CHCH); 76.13 (C=OCHCH); 65.90 (CH$_2$OC=O); 49.02 (CHO); 44.62 (CH$_2$O); 27.15 (CCH$_3$); 26.12 (CCH$_3$).

| eq | Compound | Mw (g/mol) | Density (g/ml) | Quantity (g) | Quantity (ml) | Quantity (mmol) |
|---|---|---|---|---|---|---|
| 1 | GalXallylester | 370 | — | 11.0 | — | 29.7 |
| 7 | Meta-chloroperoxybenzoic-acid (mCPBA) | 172 | — | 35.8 | — | 208 |
| — | Dichloromethane (DCM) | — | — | — | 250 ml | — |
| 1 | GalX-diepoxyester | 402 | — | 11.9 | — | 29.7 |

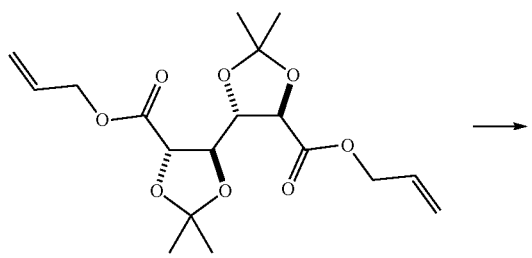

Chemical Formula: $C_{18}H_{26}O_8$
Molecular Weight: 370.40

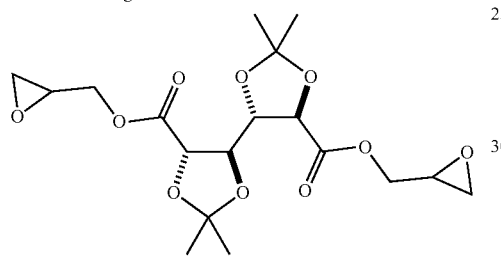

Chemical Formula: $C_{18}H_{26}O_{10}$
Molecular Weight: 402.40

Example 3: Synthesis of GalX-allylamide

Allylamine (g, 30.3 mmol) was added to a solution of GalX (5 gram, 14.5 mmol) in MeOH (50 mL). The solution was stirred for 1 night at room temperature. After evaporation of the solvent, 50 mL of ethyl acetate was added and the solution was refluxed overnight. After cooling down and evaporation, the solid material was crystallized from ethanol and water, filtrated and dried in a vacuum oven.

Product GalX-allylamide (Mw 368): 3.1 gram (yield 58%). HPLC: 99% pure material. $^1$H NMR (400.17 MHz, CDCl$_3$): δ (ppm)=6.74 (s, 2H); 5.83 (m, 2H); 5.21 (dd, $^2J_{HH}$=17.2 Hz, $^3J_{HH}$=1.4 Hz, 2H); 5.15 (dd, $^2J_{HH}$=10.2 Hz, $^3J_{HH}$=1.2 Hz, 2H); 4.79 (d, $^2J_{HH}$=7.0 Hz, 2H); 4.53 (d, $^2J_{HH}$=7.1 Hz, 2H); 3.91 (m, 4H), 1.51 (s, 6H), 1.44 (s, 6H). $^{13}$C NMR (100.62 MHz, CDCl$_3$): δ (ppm)=170.72 (C=O); 133.82 (CH$_2$=CH); 116.69 (CH$_2$=CH); 110.89 (C(CH$_3$)$_2$); δ 78.76 (CHCH); 75.01 (C=OCHCH); δ 41.35 (CH$_2$NHC=O); 26.82 (CCH$_3$); 26.11 (CCH$_3$).

| eq | Compound | Mw (g/mol) | Density (g/ml) | Quantity (g) | Quantity (ml) | Quantity (mmol) |
|---|---|---|---|---|---|---|
| 1 | GalX | 346 | — | 5 | — | 14.5 |
| 2.1 | Allylamine | 57.1 | 0.763 | 1.73 | 2.27 | 30.3 |
| — | MeOH | — | — | — | 50 ml | — |

| eq | Compound | Mw (g/mol) | Density (g/ml) | Quantity (g) | Quantity (ml) | Quantity (mmol) |
|---|---|---|---|---|---|---|
| 1 | GalX-allylamide | 368 | — | — | — | 14.5 |

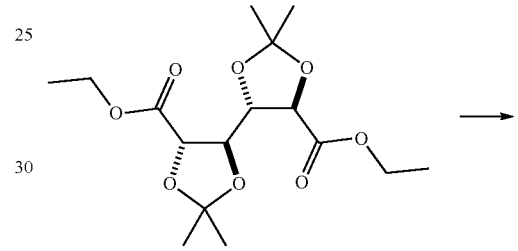

Chemical Formula: $C_{16}H_{26}O_8$
Molecular Weight: 346.38

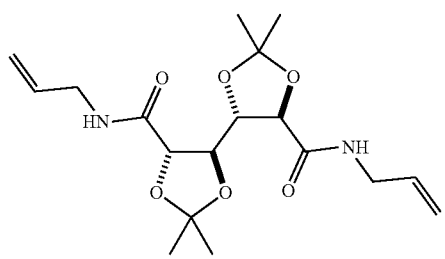

Chemical Formula: $C_{18}H_{28}N_2O_6$
Molecular Weight: 368.43

Example 4: Synthesis of GalX-diepoxyamide mCPBA (32.7 g, 190 mmol) was added to a solution of GalXallylamide (10 gram, 27.2 mmol) in DCM (250 mL). The solution was stirred for 60 hours at reflux temperature. After cooling down, the solution was filtrated. The filtrate was washed with Na$_2$SO$_3$, Na$_2$CO$_3$ and water. The organic phase was evaporated to dryness.

Product GalX-diepoxyamide crude (Mw 402): 7.1 gram (yield 65%); HPLC: 99% pure material.

| eq | Compound | Mw (g/mol) | Density (g/ml) | Quantity (g) | Quantity (ml) | Quantity (mmol) |
|---|---|---|---|---|---|---|
| 1 | GalXallylamide | 368 | — | 10.0 | — | 27.2 |
| 7 | Meta-chloroperoxybenzoic-acid (mCPBA) | 172 | — | 32.7 | — | 190 |
| — | Dichloromethane (DCM) | — | — | — | 250 ml | — |
| 1 | GalX-diepoxyamide | 402 | — | 10.9 | — | 27.2 |

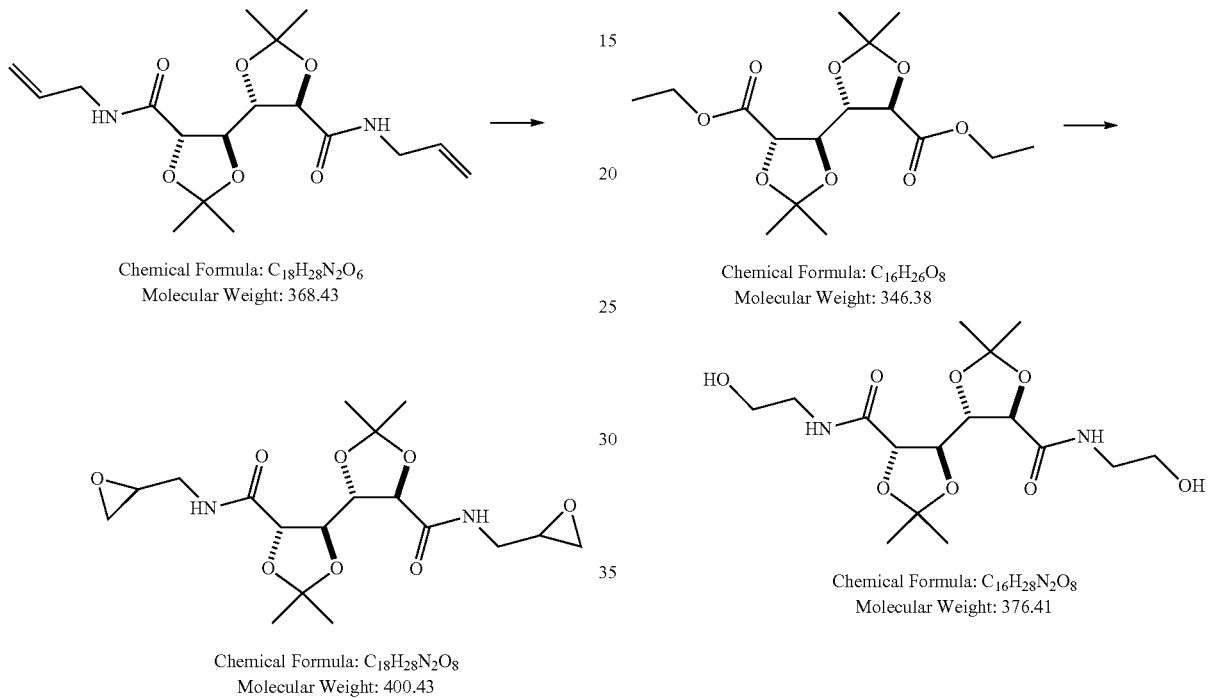

Chemical Formula: $C_{18}H_{28}N_2O_6$
Molecular Weight: 368.43

Chemical Formula: $C_{16}H_{26}O_8$
Molecular Weight: 346.38

Chemical Formula: $C_{18}H_{28}N_2O_8$
Molecular Weight: 400.43

Chemical Formula: $C_{16}H_{28}N_2O_8$
Molecular Weight: 376.41

Example 5: Synthesis of GalX-diethanolamide

Ethanolamine (43.5 ml, 0.72 mol) was added to a solution of GalX (100 gram, 0.29 mol) in EtOH (500 mL). The solution was stirred for 1 night at reflux temperature. After evaporation of the solvent, the solid material was recrystallized from ethylacetate (1 L), filtrated and dried in a vacuum oven.

Product GalX-di-ethanolamide (Mw 376): 83.6 gram (yield 77%). HPLC: 99% pure material. $^1$H NMR (400 MHz, DMSO-$d_6$) δ 7.82 (t, J=5.8 Hz, 2H), 4.68 (t, J=5.5 Hz, 2H), 4.51 (dd, J=6.3 Hz, 2H), 4.36 (dd, 2H), 3.43 (q, J=6.1 Hz, 4H), 3.29-3.10 (m, 4H), 1.41 (s, 6H), 1.35 (s, 6H). The water-solubility of the product is approximately 25 wt. % (35 gram per 100 ml water, at ambient temperature).

Example 6: Synthesis of GalX-di-(di-ethanolamide)

Di-ethanolamine (9.1 ml, 94.6 mmol) was added to a solution of GalX (15 gram, 43 mmol) in EtOH (75 mL). The solution was stirred for 1 night at reflux temperature. After evaporation of the solvent, the material was recrystallized from ethylacetate (150 mL), filtrated and dried in a vacuum oven.

Product GalX-di-ethanolamide (Mw 376): 12.6 gram (yield 63%). HPLC: 99% pure material. $^1$H NMR (400 MHz, DMSO-$d_6$) δ 4.80 (t, J=5.3 Hz, 2H), 4.70 (dd, 2H), 4.67 (t, J=5.4 Hz, 2H), 4.61 (dd, J=3.8, 1.8 Hz, 2H), 3.72-3.60 (m, 2H), 3.60-3.51 (m, 4H), 3.51-3.39 (m, 7H), 3.36-3.21 (m, 3H), 1.32 (s, 6H), 1.27 (s, 6H). The water-solubility of the product was approximately 50 wt. % (i.e. 100 gram per 100 ml water, at ambient temperature).

| eq | Compound | Mw (g/mol) | Density (g/ml) | Quantity (g) | Quantity (ml) | Quantity (mol) |
|---|---|---|---|---|---|---|
| 1 | GalX | 346.38 | — | 100 g | — | 0.29 |
| 2.5 | Ethanolamine | 61.08 | 1.012 | 44 g | 43.5 ml | 0.72 |
| — | MeOH | — | — | — | 1000 ml | — |
| 1 | GalX-di-ethanolamide | 376.41 | — | 108.6 g | — | 0.29 |

| eq | Compound | Mw (g/mol) | Density (g/ml) | Quantity (g) | Quantity (ml) | Quantity (mmol) |
|---|---|---|---|---|---|---|
| 1 | GalX | 346.38 | — | 15 | — | 43 |
| 2.2 | Diethanolamine | 105.14 | 1.09 | 9.9 | 9.1 ml | 94.6 |
| — | EtOH | — | — | — | 75 ml | — |
| 1 | GalX-di-(diethanolamide) | 464.51 | — | 20 | — | 43 |

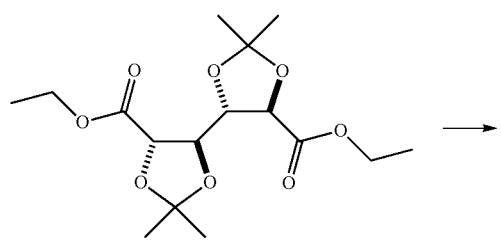

Chemical Formula: $C_{16}H_{26}O_8$
Molecular Weight: 346.38

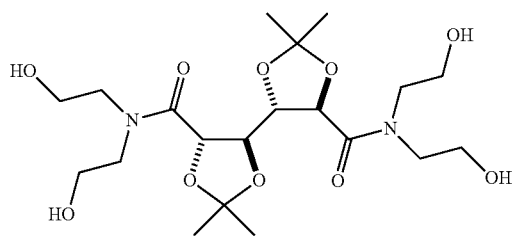

Chemical Formula: $C_{20}H_{36}N_2O_{10}$
Molecular Weight: 464.51

The invention claimed is:

1. Compound having a structure represented by formulas (Ia) and (Ib):

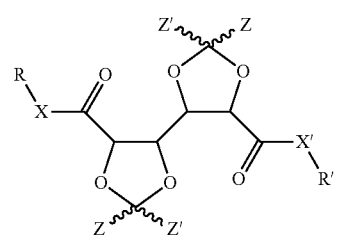

(Ia)

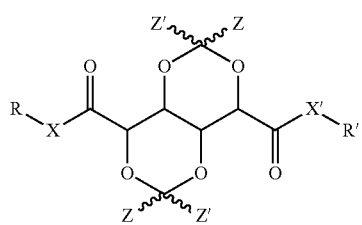

(Ib)

wherein:

X represents $NR^a$;

X' represents a heteroatom or heteroatom containing group selected from —O—, —NH— and —$NR^{a'}$—;

Z and Z' independently represent hydrogen, a straight chain or branched $C_1$-$C_4$alkyl or benzyl or the moiety Z—C—Z' represents a 5-, 6-, or 7-membered cyclic or heterocyclic group; and R, R', $R^a$ and $R^{a'}$ independently represent a reactive group containing moiety represented by the formula —($C_1$-$C_8$alkyl)-Q, wherein Q represents a reactive group and —$C_1$-$C_8$alkyl represents a branched or straight chain aliphatic alkyl group comprising 1 to 8 carbon atoms.

2. Compound according to claim 1, wherein Q represents a reactive group selected from, hydroxyl, amine, thiol, carboxyl, oxy, ethynyl, nitril, cyanate, isocyanate, thiocyanate, isothiocyanate, imine, imide, azide, nitrile, nitrite, nitro, nitroso, epoxide, cyclic carbonate, oxazoline, anhydride, acrylate and chlorotriazine.

3. Compound according to claim 1, wherein Z and Z' represent methyl.

4. Compound according to claim 1, wherein R, R', $R^a$ and $R^{a'}$ independently represent a reactive group containing moiety represented by the formula —($C_1$-$C_6$alkyl)-Q.

5. Compound according to claim 1, having the structure represented by formula (IIa):

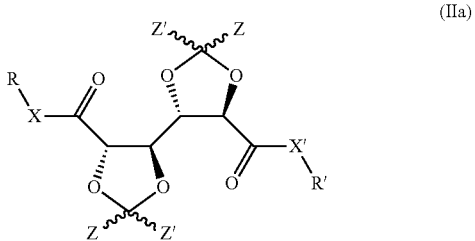

(IIa)

6. Compound according to claim 1, wherein X and X' are the same.

7. Compound according to claim 1, wherein R, R', $R^a$ and $R^{a'}$ are the same.

8. Compound according to claim 1, wherein Q represents a reactive group selected from the group consisting of epoxide and ethenyl.

9. Compound according to claim 1, wherein X represents $NR^a$—; X' represents a heteroatom or heteroatom containing group independently selected from —O—, —NH— and —$NR^{a'}$—; Z and Z' independently represent hydrogen, a straight chain or branched $C_1$-$C_4$alkyl; and R, R', $R^a$ and $R^{a'}$ independently represent a reactive group containing moiety represented by the formula —($C_1$-$C_6$alkyl)-Q, wherein —$C_{1-6}$ alkyl represents a branched or straight chain aliphatic alkyl group comprising 1 to 6 carbon atoms, and Q represents a reactive group selected from hydroxyl, amine, thiol, carboxyl, oxy, cyanate, isocyanate, thiocyanate, isothiocyanate, imine, imide, epoxide, cyclic carbonate, oxazoline, anhydride and acrylate.

10. Compound according to claim 1, X represents a heteroatom or heteroatom containing group independently selected from —O—, —NH— and —NR$^a$—; X' represents a heteroatom or heteroatom containing group independently selected from —O—, —NH— and —NR$^{a'}$—; Z and Z' independently represent hydrogen, a straight chain or branched $C_1$-$C_2$alkyl; and R, R', R$^a$ and R$^{a'}$ independently represent a reactive group containing moiety represented by the formula —($C_1$-$C_4$alkyl)-Q, wherein —$C_1$-$C_4$alkyl represents a branched or straight chain aliphatic alkyl group comprising 1 to 4 carbon atoms, and Q represents a reactive group selected from hydroxyl, amine, thiol, carboxyl, oxy, cyanate, isocyanate, imine, imide, and oxazoline.

11. Compound according to claim 1 having the structure represented by formulas (IIIf) or (IIIg):

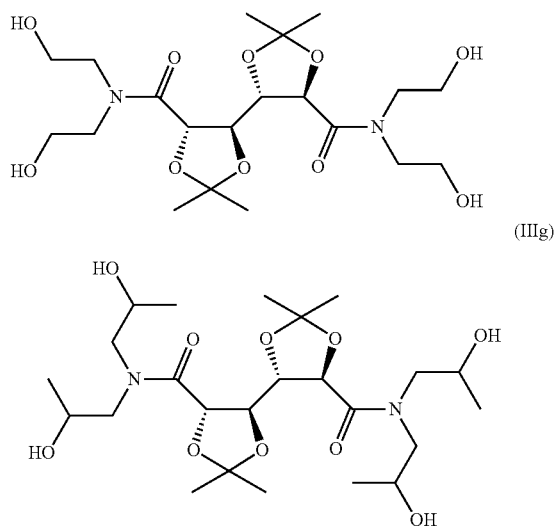

(IIIf)

(IIIg)

12. Method of producing a compound according to formula (Ia) or (Ib) as defined in claim 1, said method comprising the steps of
   a) providing a source of a C6 aldaric acid;
   b) derivatization of the C6 aldaric acid by combining the source of the C6 aldaric acid with a lower alkyl alcohol under conditions that cause the lower alkyl alcohol to react with the C6 aldaric acid carboxyl groups to form lower alkyl ester moieties;
   c) acetalisation of the esterified C6 aldaric acid as obtained in step b) by combining it with an acetalisation reagent, selected from the group of the compounds having the formula Z—C(=O)—Z' and the corresponding di-alkoxyacetals and di-alkoxyketals, wherein Z and Z' have the same meaning as defined in relation to formulas (Ia) and (Ib), under conditions that cause the acetalisation reagent to react with the aldaric acid hydroxyl groups to form the corresponding bis-dioxane or bis-dioxolane;
   d) conversion of the bis-dioxane or bis-dioxolane as obtained in step c) by reaction with a hydroxyl or amine reagent, selected from the group consisting of the compounds of formulas Q-($C_1$-$C_8$alkyl)-OH; Q-($C_1$-$C_8$alkyl)-NH$_2$ and Q-($C_1$-$C_8$alkyl)-NH—($C_1$-$C_8$alkyl)-Q, wherein Q and $C_1$-$C_8$alkyl have the same meaning as defined in relation to formulas (Ia) and (Ib), under conditions that cause the hydroxyl or amine reagent to displace the lower alkyl groups of the ester moieties of the bis-diox(ol)anes to form said compound according to formula (Ia) or (Ib).

13. Method according to claim 12, wherein the C6 aldaric acid is galactaric acid.

14. Method according to claim 12, wherein step b), wherein the acetalisation reagent is selected from the group consisting of formaldehyde, acetaldehyde, acetone, propanal, butanone, butanal, cyclohexanone, benzaldehyde and the corresponding dialkoxylated, preferably dimethoxylated, acetals or ketals thereof.

15. Method according to claim 12, wherein X and X' represent —O— and step d) comprises:
   d1) combining the bis-dioxane or bis-dioxolane with a stoichiometric excess of a hydroxyl containing reactant having the formula Q-($C_1$-$C_8$alkyl)-OH, optionally in a suitable solvent, to produce a liquid reaction mixture;
   d2) subjecting the liquid reaction mixture to conditions under which the displacement reaction proceeds.

16. Method according to claim 12, wherein X and X' represent —NH—, —NR$^a$— or —NR$^{a'}$—, and step d) comprises:
   d1') combining the bis-dioxane or bis-dioxolane with the amine containing reactant selected from the group consisting of Q-($C_1$-$C_8$alkyl)-NH$_2$ and Q-($C_1$-$C_8$alkyl)-NH—($C_1$-$C_8$alkyl)-Q in a suitable solvent, to produce a liquid reaction mixture;
   d2') subjecting the liquid reaction mixture to conditions under which the displacement reaction proceeds.

* * * * *